United States Patent [19]

Koller

[11] Patent Number: 5,128,247
[45] Date of Patent: Jul. 7, 1992

[54] METHODS FOR ISOLATION OF NUCLEIC ACIDS FROM EUKARYOTIC AND PROKARYOTIC SOURCES

[75] Inventor: Charles A. Koller, Houston, Tex.

[73] Assignee: Board of Regents, The University of Texas System, Austin, Tex.

[21] Appl. No.: 394,092

[22] Filed: Aug. 14, 1989

[51] Int. Cl.$^5$ .............. C12P 19/34; C12N 1/06; C12N 1/08; C12N 11/10
[52] U.S. Cl. .............. 435/91; 435/6; 435/259; 435/270; 435/820; 536/27; 536/28; 935/19; 935/20; 935/21
[58] Field of Search ............ 435/91, 6, 259, 270, 435/820; 530/380; 536/27, 28; 935/19-21

[56] References Cited

U.S. PATENT DOCUMENTS

| | | | |
|---|---|---|---|
| 4,407,957 | 10/1983 | Lim | 435/180 |
| 4,508,826 | 4/1985 | Foor | 435/172.2 |
| 4,828,990 | 5/1989 | Higashi et al. | 435/69.51 |
| 4,830,969 | 5/1989 | Holmes | 435/259 |
| 4,935,342 | 6/1990 | Seligson et al. | 435/91 |
| 4,968,432 | 11/1990 | Antiwiler | 530/380 |

FOREIGN PATENT DOCUMENTS 0127327 12/1984 European Pat. Off.
0215533 3/1987 European Pat. Off.

OTHER PUBLICATIONS

Bahnak, et al, "A Simple and Efficient Method for Isolating High MW DNA from Mammalian Sperm", *NAR*, 16(3):1208, 1988.

Miller, et al, "A Simple Salting Out Procedure for Extracting DNA from Human Nucleated Cells", *NAR* 16(3):1215, 1988.

Bowtell, "Rapid Isolation of Eukaryotic DNA", *Analytical Biochemistry*, 162:463-465, 1987.

Chomczynski, et al, "Single-Step Method of RNA Isolation by Acid Guanidinium Thiocyanate-Phenol-Chloroform Extraction", *Analytical Biochemistry*, 162:156-159, 1987.

Gustafson, et al, "Parameters Affecting the Yield of DNA from Human Blood", *Analytical Biochemistry*, 165:294-299, 1987.

Hoffman, et al, "A 10-Minute DNA Preparation from Yeast Efficiently Releases Autonomous Plasmids for Transformation of *Escherichia coli*", Gene, 57:267-272, 1987.

Jeanpierre, "A Rapid Method for the Purification of DNA from Blood", *NAR*, 15(22):9611, 1987.

Lippke, et al, "Isolation of Intact High-Molecular Weight DNA by Using Guanidine Isothiocyanate", *Applied and Environmental Microbiology*, 53:2588-2589, 1987.

Holm, et al, "A Rapid Efficient Method for Isolating DNA from Yeast", *Gene*, 42:169-173, 1986.

(List continued on next page.)

*Primary Examiner*—Herbert J. Lilling
*Attorney, Agent, or Firm*—Arnold, White & Durkee

[57] ABSTRACT

The present invention relates to methods and compositons for isolation of nucleic acids from cells. In particular aspects, this invention relates to the use of chaotropic compositions, such as guanidine hydrochloride or guanidinium isothiocyanate, in combination with polyanionic compositions, such as those containing sulfated polysaccharides (i.e., heparin or heparitin sulfate), for the isolation of nucleic acids (RNA or DNA). This method involves disrupting and lysing cells using a nucleic acid releasing composition containing a chaotropic component for the release of nucleic acids from the cell (guanidine hydrochloride or guanidinium isothiocyanate). The released nucleic acids are collected by ethanol precipitation and resuspended before exposure to a polyanion-containing protein dissociating composition which promotes the dissociation of nucleic acid associated proteins from the resuspended nucleic acids. The isolated nucleic acids are washed, further collected by ethanol precipitation and resuspended in a selective buffer prior to further use.

33 Claims, 1 Drawing Sheet

OTHER PUBLICATION

Krawetz, et al, "Isolation and Fractionation of Total Nucleic Acids from Tissues and Cells", *J. of Biochemical and Biophysical Methods*, 12:29–36, 1986.

Cathala, et al, "A Method for Isolation of Intact, Translationally Active RNA", *DNA*, 2(4):329–335, 1983.

Bornens, et al, "Isolation of Nuclear Envelopes with Polyanaions", *J. of Cell Biology*, 76:191–206, 1978.

Hildebrand, et al, "Action of Heparin on Mammalian Nuclei, II. Cell-Cycle-Specific Changes in Chromatin Organization Correlate Temporally with Histone H1 Phosphorylation", *BBA*, 517:486–499, 1978.

Janakidevi, K., "Effect of Heparin or Removal of Lysine-Rich Histone Fraction on the Poly(AD-P-Ribose) Polymerase, DNA Polymerase and Template Activity of Isolated Swine Aortic Nuclei", *Exp. Cell Research*, 112:345–351, 1978.

Hildebrand, et al, "Preparation of Nuclear Membranes from Cultured Chinese Hampster Cells by Heparin Treatment", *Abstract form*, about 1973.

Bornens, M., "Action of Heparin on Nuclei: Solubilization of Cromatin enabling the Isolation of Nuclear Membranes", *Nature*, 24:28–30, 1973.

Kinoshita, S., "Heparin as a Possible Initiator of Genomic RNA Synthesis in Early Development of Sea Urchin Embryos", *Exp. Cell Research*, 64:403–411, 1971.

Noll, et al, "The Use of Sodium and Lithium Dodecyl Sulfate in Nucleic Acid Isolation", *Methods in Enzymology*, vol. XII, *Nucleic Acids*, Part B, pp. 129–160.

Lai, et al, "Pulsed Field Gel Electrophoresis", *Biotechniques*, 7 (1), 34–42, Jan. 1989.

International Search Report.

Article by Jang H. Han et al., entitled "Isolation of Full-Length Putative Rat Lysophospholipase cDNA Using Improved Methods for mRNA Isolation and cDNA Cloning," *Biochemistry*, vol. 26, pp. 1617–1625 (1987).

Article by Judith A. Lippke et al. entitled "Isolation of Intact High-Molecular-Weight DNA by Using Guanidine Isolthiocyanate," *Applied and Environmental Microbiology*, vol. 53, No. 10, pp. 2588–2589 (1987).

METHODS FOR ISOLATION OF NUCLEIC ACIDS FROM EUKARYOTIC AND PROKARYOTIC SOURCES

BACKGROUND OF THE INVENTION

The government may own certain rights in the present invention pursuant to NIH grant No. 177590.

1. Field of Invention

The present invention relates to methods and compositions for isolation of nucleic acids from cells. In particular aspects, this invention relates to the use of chaotropic compositions, such as guanidine hydrochloride or guanidinium isothiocyanate, in combination with polyanionic compositions, such as those containing sulfated polysaccharides (heparin), for the isolation of nucleic acids (DNA or RNA).

2. Description of the Related Art

Techniques for isolating nucleic acids from cells have been employed for many years. With the increasing importance of molecular biology, biochemistry, virology and cellular biology, along with the recent technological advances in these disciplines, the need for isolated quality nucleic acids has increased considerably. It is not sufficient to now merely ,isolate, nucleic acids prior to their utilization in different experiments. The isolation of nucleic acids is one important initial step in any protocol where the use of nucleic acids is envisioned, whether it be DNA or RNA. In fact, the success of an entire experimental protocol may lie in the initial steps of isolating quality nucleic acids.

Thus, within the last few years, it has been an aim of molecular biologists to identify isolation procedures for nucleic acids which yield quality material in acceptable quantities. An important 'quality' of the isolated nucleic acid is that the product be essentially free of contaminating substances which might otherwise interfere with subsequent experimental manipulations. For example, the contaminating substances may be proteins or residual compounds or chemicals used during the isolation procedure.

It is particularly desirable to isolate nucleic acids that are relatively intact and thus not appreciably degraded. This is important where one seeks to obtain nucleic acids in excess of 10 kilobases. Nucleic acid isolation often precedes a tedious experimental protocol which, more than likely, will require extensive handling and manipulations of the nucleic acids. However, it is often difficult to isolate intact, high molecular weight DNA (size in excess of 15 kilobases) because the size of the DNA itself imposes inherent handling problems (1-3). With this information in mind, and in order to improve recovery of amount of nucleic acid isolated, as well as quality, handling and processing time for isolating nucleic acids are a concern when developing new protocols.

Once isolated, nucleic acids will typically need to be dissolved in a buffer of choice. If the isolated nucleic acids is not capable of being dissolved in the required buffer system, then even relatively intact and purified nucleic acids will not be useful. Difficulties in resuspending the isolated nucleic acid product have presented problems (4). Thus, nucleic acid isolation methods should reproducibly generate intact nucleic acids which are essentially free of contaminating substances, which will dissolve in a selective buffer and are, therefore, functional in a variety of different experimental designs (restriction enzyme analyses, cloning into specific vectors, mutating by point mutation, etc.).

Enzymes are often employed to assist in purifying nucleic acids free of associated macromolecules, such as protein, lipids, etc. However, the use of enzymes (pronase, RNAse, DNAse, etc.) to selectively eliminate one component involves a risk factor that is difficult to measure. For example, elimination of RNA from DNA samples will require the use of specially purified RNAse that are 'essentially DNAse free'. Thus, a valuable sample of DNA is potentially at risk of becoming degraded where even minute amounts of DNAse remain in the RNAse.

Inactivating nucleases, inherent components of most cells, present another problem with which the investigator must deal with. When cells are disrupted, nucleases are released which will tend to degrade the nucleic acid sought to be isolated. A variety of denaturants (e.g., urea, SDS, guanidine hydrochloride and guanidinium isothiocyanate) have been employed with varying degrees of success to inactivate endogenous nucleases and proteases (5-11). Unfortunately, these agents alone have not been shown to provide isolated nucleic acids of the highest quality.

As noted, it is not uncommon to isolate nucleic acids which are degraded due to the extensive handling required by the individual protocol. The average size of DNA obtained from currently available isolation protocols is typically on the order of about 20-40 kilobases (2,3,7). A protocol which would eliminate some handling would thus offer an advantage over existing protocols. Also, a protocol which would allow for the isolation of even higher molecular weight nucleic acids (e.g., greater than 75 kilobases) would be useful for a variety of different experimental approaches (preparation of cosmid libraries, etc).

Organic solvents, such as phenol have also been utilized to aid in the elimination of proteins. Organic solvents are helpful in nucleic acid purification protocols, but present a tedious problem in terms of safety as well as in eliminating traces of remaining solvents. These solvents may retard the dissolution of the nucleic acid into an appropriate buffer as well as hinder further enzymatic manipulation of the nucleic acid (4,11).

In light of these and other drawbacks in the prior art for isolating nucleic acids, there is a need for an isolation method which is generally applicable to numerous cell types, as well as reproducible, efficient and inexpensive. The invention disclosed herein presents methods and compositions which allow for the timely, efficient, inexpensive and straightforward purification of nucleic acids without worry of degradation, elimination of wrong components, or producing a product which will not be functional in further experimentation. The invention described herein relates to the efficient purification of high molecular weight nucleic acids (often greater than 75 kilobases) which are relatively free of unwanted components, are essentially intact, are usually able to dissolve in an appropriate buffer system, and are thereby functional in a variety of experimental protocols ranging across many different disciplines of research.

SUMMARY OF THE INVENTION

In its broadest scope, the present invention provides a method for the isolation of nucleic acids from a variety of cell sources. This method includes the use of compositions which release and dissociate proteins from nucleic acids. More particularly, the present invention describes a method of nucleic acid isolation which involves the novel use of nucleic acid releasing and protein-dissociating compositions at a level effective to promote the release of nucleic acid-associated proteins. The nucleic acids obtained from this invention will generally be relatively intact and essentially free from contaminating components. Further, they dissolve in a selective buffer and are thereby functional in a variety of protocols.

Employing this invention for the isolation of nucleic acids yielded unexpected and surprising results, in that many of the foregoing limitations are routinely eliminated. Combining a chaotropic composition along with a polyanion containing protein dissociating component produces quality nucleic acids from a variety of sources. The methods and compositions described herein have also been found to be efficient and rapid, as well as straightforward. Although the techniques of this invention do not require extensive equipment or technical experience, they are readily adaptable to automation.

A method and specific compositions for isolating nucleic acids from cells are detailed. In general, this method involves disrupting and lysing cells using a nucleic acid releasing composition containing a chaotropic component for the release of nucleic acids from the cell. The released nucleic acids are collected by precipitation, such as with ethanol, and resuspended prior to exposure to a polyanion-containing protein dissociating composition. This polyanion-containing protein dissociating composition promotes the dissociation of nucleic acid associated proteins from the resuspended nucleic acids. The isolated nucleic acids are further collected by precipitation, washed and resuspended in a selective buffer prior to further use. Collecting the nucleic acids may be further accomplished by centrifuging the ethanol precipitated nucleic acids.

In accordance with the present invention, nucleic acids may be isolated from either eukaryotic or prokaryotic systems. The source of nucleic acids isolated from a eukaryotic system ranges from blood components to solid tissue biopsy samples. The efficacy of the method presented herein does not generally depend on the source of the cells. However, it is contemplated that this protocol will prove effective with a wide range of cell types and sources from different species, tissues and the like.

In accordance of this invention, the phrase nucleic acids shall be defined to comprise either deoxyribonucleic acid (DNA) or ribonucleic acid (RNA) or both. In certain instances where specific identification is required, the individual terms DNA or RNA shall be used. If the specific identification is not required then the general phrase nucleic acids will be employed.

Although advantages will be realized without the use of enzymes, enzymes can be employed to specifically eliminate RNA or DNA (defined as RNAse or DNAse, respectively). Furthermore, there are a number of different proteases known to those skilled in the art which effectively digest proteins. While any one of these are suitable for protein digestion, optimum results are obtained with proteinase K (e.g., in a 0.5% vol/vol sarcosyl solution, about 100 micrograms/ml, 30-60 minutes at 37° C.).

Disruption and lysing of cells is achieved in accordance with the invention through the use of a nucleic acid releasing composition containing a chaotropic component. As used herein, the phrase 'nucleic acid releasing composition containing a chaotropic component' refers generally to chemical compositions which effectively promote the release of nucleic acids and proteins by dissolving the cells through the action of disruption and lysis. The nucleic acid releasing composition will preferably contain a chaotropic agent, salt, detergent and a reducing agent. However, many of the individual, major compounds found in the nucleic acid releasing composition will often be a matter of choice, as discussed below.

Of particular interest to this overall disclosure is the release of nucleic acids and proteins, as well as endogenous proteases and nucleases, which occurs during the disruption and lysis of the cells. During the initial disruption and lysis step, the endogenous proteases and nucleases should be effectively and instantaneously inactivated. This inactivation is necessary for protecting the released nucleic acids from rapid degradation. Inactivation of the endogenous proteases and nucleases is achieved through the inclusion of a chaotropic component in the nucleic acid releasing composition.

The chaotropic component of the nucleic acid releasing composition is both an effective protein denaturant and a strong inhibitor of nucleases. The effect of a chaotropic agent on growing cells is an almost instantaneous dissolution of the cells. Typically chaotropic agents useful in the practice of the invention include guanidine hydrochloride, guanidinium isothiocyanate and urea. Agents having chaotropic capability which are useful in releasing nucleic acids from chromatin structures will generally be familiar to those skilled in the art. While all the foregoing chaotropic agents will provide advantages in accordance with the invention, the use of guanidinium isothiocyanate or guanidine hydrochloride is particularly preferred for optimum nucleic acid isolation.

Effective concentrations for the above compounds are generally known to those familiar with the art. Usually, the molarities of guanidine-containing chaotropic agents effective for cellular disruption and lysis range from concentrations of about 3M to about 7M guanidine. In the inventors' hands, optimum results are typically obtained with about 4M guanidinium isothiocyanate. However, the use of other chaotropic components in the known ranges would also be effective.

In certain embodiments, and particularly with regard to the nucleic acid releasing composition, it will often prove beneficial to incorporate a surface-active anionic detergent to further aid in lysis and disruption of the cells. The type of anionic detergent included in this solution is not critical, and to those skilled in the art, it is apparent that either sarcosyl, sarcosine, sodium dodecyl sulfate (lauryl sulfate) or lithium dodecyl sulfate would likely prove equally as effective.

A further component which may be included in the nucleic acid releasing composition is a sulfhydryl reducing agent which aids in the disruption and lysis of the cells, as well as the dissociation of the proteins from the nucleic acids. A variety of different sulfhydryl reducing agents may be employed, with mercaptoethanol or dithiothreitol (DTT) being preferred.

Typically, the nucleic acid releasing composition will further include salt, at a concentration effective to aid in the dissociation, purification and eventual dissolution of the isolated nucleic acids. Salt concentrations ranging from about 0.1M to about 0.9M are generally effective in dissociating proteins from nucleic acids. Optimum results are usually obtained with a salt concentration of about 0.4M to 0.6M. The type of salt included in the nucleic acid releasing composition is not critical. For example, sodium chloride, sodium acetate, potassium acetate, ammonium acetate or other derivatives thereof, would suffice, however, optimum results are obtained with either sodium chloride or sodium acetate.

As noted, the method of this invention further involves the use of a polyanion-containing protein-dissociating composition to promote the effective dissociation of the resuspended nucleic acids from the proteins. This composition is comprised generally of a sulfated polysaccharide containing a polyanion component. The effective concentrations of the sulfated polysaccharide will preferably range from about 0.1 to 1.0 milligram per milliliter. Optimum concentrations for the sulfated polysaccharide will be more or less in the range of the concentration of DNA in the sample (e.g. from 0.2 to 1.2 milligram per milliliter). The preferred sulfated polysaccharide polyanion for use in the practice of the invention is heparin. However, other sulfated polysaccharides are known in the art and it is proposed that these alternatives will provide benefits in accordance with the invention. For example, heparitin sulfate (heparan sulfate), would also suffice in the polyanion-containing protein-dissociating composition. With regard to heparin, the particular salt employed in not believed to be particularly crucial. However, preferably either the sodium or lithium derivative is employed, with lithium being preferred.

In certain further embodiments, the polyanion-containing protein-dissociating composition will further include a phosphate source (preferably sodium derivative) in the range of about 10 to 25 mM. The inclusion of phosphate aids in solubilizing of the chromatin, often 95% or more. Less rapid and incomplete solubilization is obtained with potassium salt. Sulfate components, ATP and GTP may also be effective in aiding in the solubilization of chromatin. However, for optimal chromatin solubilization, the polyanion-containing protein-dissociating composition should contain phosphate in concentrations ranging from 2 mM to 10 mM.

DNA was isolated from about $5 \times 10^6$ K562 cells or from leukapheresis samples of peripheral blood cells according to the protocol presented in the Detailed Description of the Invention. K562 cell line was derived from a Philadelphia chromosome positive patient with chronic myelogenous leukemia in blast crisis (12). The peripheral blood was obtained from patients, with one form of leukemia, from the Department of Hematology, M.D. Anderson Hospital and Tumor Institute. The DNA was separated on a 1% agarose gel and the buffer system was TAE (0.04M Tris Acetate, 0.001M EDTA, pH 8.0). The DNA was stained with etidium bromide (500 micrograms per liter) in $1 \times TAE$ and photographed under ultraviolet light. The molecular weight markers in lanes 1 and 8 are Hind III digested lambda DNA: 23.1 Kb, 9.4 Kb, 6.6 Kb, 4.4 Kb, 2.3 Kb, 2.0 Kb and 0.56 Kb, as well as Hae III digested $\phi \times 174$ DNA: 1.35 Kb, 1.08 Kb, 0.87 Kb, 0.60 Kb, 0.28 Kb and 0.23 Kb, respectively. Lanes 2 and 3 are undigested K562 DNA, lanes 4 through 7 are undigested DNA obtained from leukapheresis samples of peripheral blood cell from patients WC, EF, RL and RM.

Figure 2:
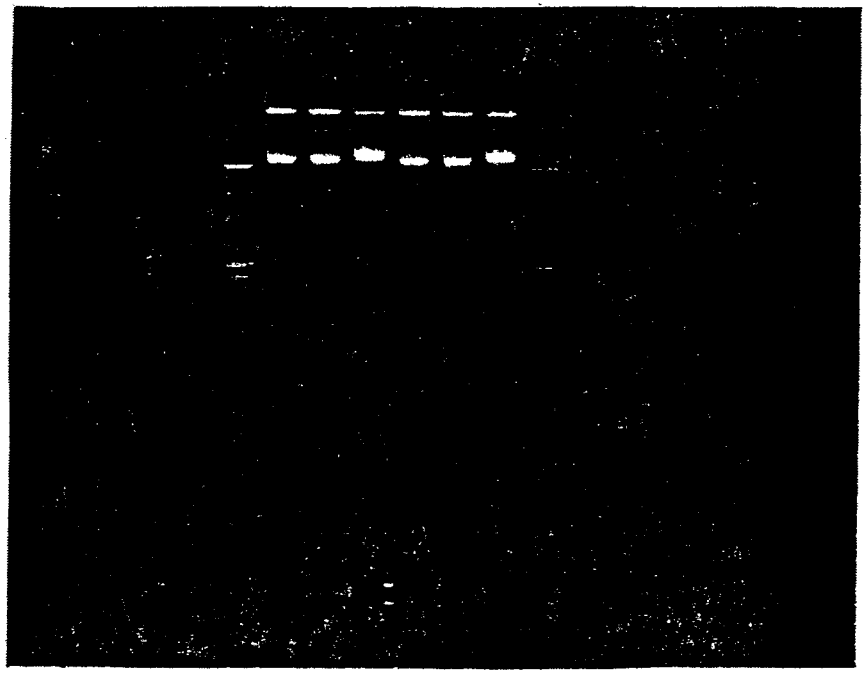

FIG. 2. Restriction Enzyme Digestion of Human Genomic DNA

The isolated DNA was digested with a predetermined restriction enzyme overnight at 37° C. The restricted DNA was then separated on an agarose gel (0.7%) and run in TAE buffer at 20 volts for 17 hours. The DNA was stained with ethidium bromide (500 $\mu l/1$ in $1 \times TAE$) and photographed under ultraviolet light. Hind III digested lambda DNA and Hae III digested $\phi \times 174$ were used for molecular weight markers.
Lanes 1 and 2 Molecular Weight Markers
Lanes 3 DNA 'EF' Digested with BamH I
Lane 4 DNA 'EF' Digested with Bg2II
Lane 5 DNA 'EF' Digested with EcoRI
Lane 6 DNA 'EF' Digested with Hind III
Lane 7 DNA 'EF' Digested with Pst I
Lane 8 DNA 'EF' Digested with Pvu II

DETAILED DESCRIPTION OF THE INVENTION

Overview of Procedure for Nucleic Acid Isolation

As noted, the practice of the invention is believed to be applicable to the isolation of any nucleic acid polymer, regardless of source or amount of material to work with. Due to the relative ease and efficiency of isolation using the present technique, the invention will likely find particular application in the isolation of nucleic acids where only minute amounts of materials are available. Set forth below is a preferred protocol for practicing the isolation technique of the invention, set forth in a manner which is directly applicable to isolation starting with a relatively small sample, e.g., about 0.5 to 5 million cells or so. Where larger samples are employed one will desire to simply increase the proportions of materials accordingly. Of course, in light of the following disclosure, those of skill will recognize that many modifications can be made in this procedure and nevertheless obtain benefits in accordance with the invention.

In the practice of preferred aspects of the invention, about 0.5 to $5 \times 10^6$ cells are dissolved in 400 microliters of the nucleic acid releasing composition (solution I). For larger amounts of starting material, the cells or tissue should be dissolved in a 4% volume/volume or weight/volume solution of the releasing composition employed. One will generally dissolve the cells in the releasing composition by simply swirling them in the releasing composition in a manner to achieve a uniform disruption and dissolution of cellular debris. Optimal results are obtained when the cells are dispersed or suspended in a small volume (e.g., up to about 1/10 volume) of physiological saline. However, certain cells may be particularly difficult to disrupt, such as yeast, bacteria or plants. In such instances, more strenuous mechanical assistance, such as vortexing or even homogenization, may be needed. Improved dissolution of bacterial cells may be effected by the addition of 1/10 volume of 10 N NaOH for 5 minutes with gentle swirling followed by the addition of 1/10 volume glacial acetic acid and centrifugation of the precipitate.

Once solubilized in the releasing compositions, the nucleic acid is found to be particularly stable, probably due to the highly chaotropic nature of the releasing composition employed which effectively inhibits degrading enzymes as well as microbial growth. It is believed that the lysed cells can be stored, preferably in the dark, at room temperature up to 6-8 months and perhaps longer without degradation of nucleic acids.

Once the cells have been solubilized to the extent possible in the releasing composition, it may be found for certain cell types or nucleic acid sources such as plants or yeast that there may be some degree of insoluble debris. In these instances, one will probably desire to remove any such insoluble debris. This can most readily be achieved by simply centrifuging the mixture to a degree that will pellet any such debris. Centrifugation will generally prove the easiest and most effective means of removing debris, but other means can be employed.

One will then desire to remove the solubilized nucleic acids from the solution by precipitation. Precipitation is a fairly important aspect of the invention in that, due to the ability to more or less preferentially precipitate nucleic acids as opposed to other cellular components such as proteins, it results in a significant purification of nucleic acids. Precipitation of DNA is most readily achieved by the addition of room temperature absolute ethanol, for example, at a level of about 2.5 volumes (thus making the solution about 70% ethanol). While ethanol precipitation is preferred, there are likely other means of precipitation which can be employed where desired, such as the addition of room temperature 2-propanol (isopropanol), at a level of about 1 volume (thus making the solution about 50% isopropanol). The precipitation is initiated by rocking the tube to gently mix the two solutions. Interestingly, the inventor has found that precipitation at room temperature is quite effective, and avoids potential problems of precipitation of RNA and proteins.

The precipitated material can then be collected by standard techniques such as decanting or pipetting off the supernatant. For smaller amounts of starting materials, the precipitated nucleic acids may be collected by simply centrifuging this preparation in a standard low speed blood bank centrifuge. Of course, centrifugation is not crucial and if done excessively may actually cause DNA to clump. Other separation techniques may be employed for removing the precipitated nucleic acids, including even manual removal of the supernatant with a pipette, e.g., where larger amounts of materials are being dealt with.

Following precipitation, the liquid is decanted or aspirated off and the tube containing the precipitated DNA is inverted and allowed to drain on its side to allow the substantial removal of the alcohol-dissolving solution containing the solubilized cell components. Usually, no more than 5 minutes is required. This preparation does not need to be dried because drying will both concentrate any contaminants and also render the DNA more difficult to solubilize because of compacting.

For the purposes of RNA isolation, after cells have been solubilized in the nucleic acid releasing composition and the DNA precipitated by the addition of 2½ vol ethanol at room temperature and removed, the remaining solution of solubilized cells, in approximately 70% ethanol, is placed at −20° C. for approximately one hour and the RNA precipitated by centrifugation at 10,000 g for 15 minutes at 4° C. Immediately after removal of DNA, the yield of RNA in some types of samples can be improved by lowering the pH, for example by addition of acid, such as glacial acetic acid at from 1/50 v/v to 1:3 v/v.

After precipitation, the RNA is redissolved in the releasing composition, reprecipitated within 2 to 2½ vol ethanol at −20° for one hour then the RNA is repelleted by centrifugation at 10,000 g×15 min. at 4° C. At this point, the RNA can be treated in a variety of manners which are most consistent with its ultimate use: (1) it can be washed twice in cold 70% ethanol, sedimented and dried and resuspended in DEP treated water or the buffer of choice; (2) it can be dissolved in a modified polyanion solution (called Solution II-R) which is 1 mM EDTA, pH8; 10 mM Na phosphate, pH 7.2; and 500 μg/ml lithium heparin (e.g., Sigma Type IV) in diethyl pyrocarbonate (DEP) treated water, precipitated by the addition of 2½ vol high-salt ethanol (Solution III), cooled to −20° C. for one hour, centrifuged at 10,000 g×15 minutes at 4° C., then washed twice in cold 70% ethanol, sedimented, dried and resuspended in DEP treated water or the buffer of choice; or (3) it can be dissolved PK buffer (0.1M Tris-Cl, pH7.4, 50 mM NaCl, 10 mM EDTA, 0.2% SDS), treated with proteinase K to a final concentration of 200 μg/ml for 1-2 hours at 37° C., heated to 60° C., then 0.5 vol 60° C. water saturated phenol is added, followed by 0.5 vol chloroform/isoamyl (24:1), mixed for 10 minutes at 60° C., cooled on ice, centrifuged at 2000g×10 minutes at 4° C., reextracted again with phenol/chloroform-isoamyl alcohol at 60° C., twice with chloroform-isoamylalcohol at room temperature, precipitated with 2 1/2 vol ethanol, washed x 2 in 70% ethanol and resuspended in DEP treated water or buffer of choice.

For DNA, once the excess ethanol has been removed from the DNA, the material is dissolved in the polyanion-containing protein dissociating composition. This step is an important aspect of the invention because at this point the DNA will still tend to have a significant amount of proteins and/or chromatin material associated with it. To accomplish the polyanion-mediated protein dissociation, one will desire to dissolve the nucleic acid sample in about 1 volume of the polyanion-containing protein-dissociating solution (e.g., solution II) by gentle swirling. (Thus, where the starting cells were brought up originally in about 400 microliters of solution I, one will desire to employ about 400 microliters of solution II at this step). The weight of the Li-heparin in the DNA/Solution II should approximate the weight of DNA therein.

At this point, one may occasionally desire to employ one or more enzyme treatments to assist in removing unwanted materials. For example, where one desires to isolate DNA, one may desire to employ a DNAse-free RNAse in order to assist in the removal of RNA. Additionally, to remove proteins, a protease such as pronase or proteinase K treatment may be employed. If a protease digestion is employed, it has been found to be preferred to include a detergent such as SDS at a concentration of about 0.1% vol/vol. Techniques for the carrying out of such digestions are well known to those of skill in the art. Of course, where one desires to employ both a nuclease and protease, it will generally be desirable to conduct the nuclease treatment prior to the protease treatment, to take advantage of the proteases ability to assist in removing the nuclease.

After dissolution of the nucleic acid in the dissociating composition, and any enzymatic digestion which may be desired, the nucleic acids are then again precipitated by the addition of high salt in ethanol followed by gently mixing. The supernatant is then decanted. Centrifugation at 500 g or less for 1 min. or less may e helpful in recovering DNA from very small samples. The DNA is then washed in a lower concentration of salt in ethanol and then in aqueous ethanol. Finally, the DNA is suspended in water or buffer of choice using gentle rocking if necessary to aid in dissolution.

Should the resuspended DNA be too dilute to be useful, the DNA can again be reprecipated by the addition of about 2 volumes of high salt ethanol solution, washed with low salt ethanol, followed by aqueous ethanol. It is then redissolved in an appropriately smaller volume. The sample of isolated nucleic acids is now ready for further experimentation.

EXAMPLES

The examples which follow are illustrative of laboratory techniques found by the present inventor to constitute preferred modes for practicing various aspects of the invention. However, those of skill in the art, in light of the present disclosure, will appreciate that various modifications and alterations can be made in the structuring and carrying out of the invention, and still remain within the spirit and scope of the invention.

The materials and methods listed below were employed in carrying out the studies reported in the particular enumerated examples which follow.

Procedure for DNA Isolation

1. Five $\times 10^5$ to $1 \times 10^7$ cells are dissolved in about 400 microliters of Solution I (Nucleic Acid Releasing Composition). For larger amounts of material (e.g., white blood cells from persons with leukemia, leukapheresis samples, or solid tissue) $3 \times 10^7$ cells per ml Solution I or a 4% solution (vol/vol or wt/vol) of cells or minced tissue is prepared using Solution I (gently rocking at room temperature (RT)). It is believed that the lysed cells can be stored in the dark at room temperature for up to several months without appreciable degradation.

2. Assuming a starting volume of 400 $\mu$l, about 2.5 volumes of room temperature absolute ethanol (i.e., about 1 ml) is added to precipitate DNA. The tube is rocked for 30 seconds to gently mix the two solutions.

3. For very small amounts of starting materials, the nucleic acids may be collected by spinning this preparation in a standard blood bank centrifuge (e.g., Scientific Products, Model #C1387), 500X, 1 minute, room temperature. The liquid is then decanted or aspirated off and the tube with the collected nucleic acid allowed to drain on its side for 2-5 minutes (do not dry under vacuum).

4 Then, about 1 volume (i.e., 400 microliters) of Solution II (Polyanion-Containing Protein-Dissociating Composition) is added and the mixture gently swirled to allow the contents to dissolve.

5. For routine Southern blotting, Option 1 and Option 2, shown below, are not necessary. However, for other uses these options may be advantageously employed:

OPTION 1. Add 100 $\mu$g/ml DNAse free RNAse, incubate at 37° C., 30-60 minutes.

OPTION 2. Add ¼ vol 5x PK buffer (0.5M Tris-Cl pH 7.4, 0.25M NaCl, 0.05M EDTA, 1% vol/vol SDS), proteinase K (100-200 $\mu$g/ml.), incubate at 37° C., 30-60 minutes.

6. About 2 volumes (i.e., 800 microliters) of Solution III (0.5M Na Acetate in 75% ethanol) is then added, and the mixture rocked gently to precipitate the desired DNA. For very small concentrations of starting material, the collection of the precipitated DNA may be facilitated if the sample is centrifuged as described in Step 3.

7. The precipitated DNA is then washed two times with 800 microliters (2 volumes) of Solution IV (0.075M Na Acetate in 75% ethanol). If needed in order to collect the precipitated material, the centrifugation may be repeated.

8. The precipitated nucleic acid is then washed one time with 800-1200 microliters (2-3 volumes) of 70% ethanol. If needed, the centrifugation is repeated.

9. The precipitated nucleic acid is then dissolved in an appropriate amount of a desired buffer, such as IX TE (10 mM Tris, 1 mM EDTA pH8) or water. The preparation can be placed on a rocker or incubated at room temperature (or 37° C.) for about 10-60 minutes to allow dissolution of the precipitated nucleic acid. The nucleic acid is now ready for further analysis.

Solutions Employed for Nucleic Acid Isolation Procedure

SOLUTION I NUCLEIC ACID RELEASING COMPOSITION
  4M guanidinium isothiocyanate
  25mM Na Citrate pH 7.0
  0.5% sarcosyl
  0.1M mercaptoethanol
  0.5M Na Acetate SOLUTION II POLYANION-CONTAINING PROTEIN-DISSOCIATING COMPOSITION
  10mM EDTA pH 7.6
  10mM Na Phosphate pH 7.2
  500$\mu$g/ml lithium heparin (Sigma Type IV)

SOLUTION III
  75% ethanol
  0.5M Na Acetate

SOLUTION IV
  75% ethanol
  0.075M Na Acetate

SOLUTION V
  absolute ethanol (room temperature)

SOLUTION VI
  70% ethanol (room temperature

SOLUTION VII
  DNAse free RNAse

SOLUTION VIII
  RNAse free DNAse

SOLUTION IX
  proteinase K

Chemical Formulations of Solutions for Nucleic Acid Isolation Procedure

SOLUTION I NUCLEIC ACID RELEASING COMPOSITION
  250 g guanidinium isothiocyanate
  293 mls H$_2$O
  17.6 mls 0.75M Na Citrate pH 7.0
  26.4 mls 10% sarcosyl
  35.9 g Na Acetate Heat to 65° C. to dissolve. Solution I is completed by adding 0.72 ml mercaptoethanol/100 ml stock. This completed Solution I is stable for one month at room temperature.

SOLUTION II POLYANION-CONTAINING PROTEIN-DISSOCIATING COMPOSITION
  2 ml 0.5M EDTA pH 7.6
  1 ml 1M Na Phosphate pH 7.2
  or 0.8 ml 1M Na$_2$HPO$_4$ and 0.2 ml 1M NaH2P04
  92.5 ml H$_2$O
  50 mg lithium heparin SOLUTION III
  25 ml 2M Na Acetate
  75 ml absolute ethanol

SOLUTION IV 25 ml 0.3M Na Acetate
75 ml absolute ethanol

SOLUTION VII
DNAse free RNAse 100 µg/ml (Cat no 109142 Boehringer Mannheim Biochemicals or equivalent (BMB))

SOLUTION VIII
RNAse free DNAse (BMB Cat No. 776785)

SOLUTION IX
Proteinase K 100 µg/ml (BMB Cat. No. 161519)

EXAMPLE 1

Comparison of $A_{260}/A_{280}$ Ratios and Amount of Recovered DNA from Either One or Five $\times 10^6$ K562 Cells DNA was isolated from ranges of from 0.5 or $1 \times 10^6$ K562 cells according to the above described protocol. The isolated DNA was resuspended in water and the absorbance at 260 nm, 280 nm and 320 nm was determined in a standard spectrophotometer. The data, averaged for several experiments, is presented in Table I.

When the starting amount of cells is $1 \times 10^6$ (as determined by a hemacytometer or by Coulter counter), the spectrophotometric readings for $A_{260}$, $A_{280}$ and $A_{320}$ were reproducible as determined by the amount of variance observed from reading to reading. A low variance was also observed when determining the amount of DNA recovered from $1 \times 10^6$ cells ($+/-7$ µg). The average $A_{260}/A_{280}$ ratio observed from $1 \times 10^6$ cells was 1.72. This is indicative of little remaining residual protein in the DNA preparations. The average amount of recovered DNA isolated from $1 \times 10^6$ cells was 25 µl per million cells.

When isolating DNA from $0.5 \times 10^6$ K562 cells, according to the protocol described above, the reproducibility was maintained from one experiment to another when analyzing the amount of recovered DNA and the $A_{260}/A_{280}$ ratio. The amount of recovered DNA was 23.9 µl per $1 \times 10^6$ K562 cells. This amount was similar to the that which was recovered from $1 \times 10^6$ cells. The $A_{260}/A_{280}$ ratio obtained when isolating DNA from $0.5 \times 10^6$ cells was almost identical to the ratio obtained when isolating DNA from $1 \times 10^6$ cells (Table I). This indicated that the yield of recovered DNA was similar regardless of the starting amount of cells.

TABLE I $A_{260}/A_{280}$ RATIOS AND AMOUNT OF RECOVERED DNA FROM 1 AND $0.5 \times 10^6$ K562 CELLS

| | | |
|---|---|---|
| Starting cell number | $1 \times 10^6$ | $0.5 \times 10^6$ |
| number of isolations | 12 | 3 |
| $A_{260}$ nm | 0.334 +/− 0.094 | 0.159 +/− 0.004 |
| $A_{280}$ nm | 0.193 +/− 0.062 | 0.093 +/− 0.003 |
| $A_{260}/A_{280}$ nm | 1.72 | 1.71 |
| $A_{320}$ nm | 0.041 +/− 0.022 | 0.017 +/− 0.004 |
| DNA per total volume | 25.0 +/− 7.0 µg | 11.9 +/− 0.3 µg |
| DNA per million cells | 25.0 +/− 7.0 µg | 23.9 +/− 0.6 µg |

EXAMPLE 2

Analysis of Isolated DNA from K562 Cells and Peripheral Blood Cells

Figure 1:
FIG. 1. Analysis of Isolated DNA from K562 Cells and Peripheral Blood Cells

DNA was isolated from $1 \times 10^6$ K562 cells or from 7 mls of leukaphoresis samples of peripheral blood cells according to the above described protocol. The isolated DNA was separated on a 1% agarose gel, stained with ethidium bromide and photographed under ultraviolet light. The amount of degradation as well as contaminating RNA in this preparation of DNA was determined by carefully analyzing the gel. As was observed in FIG. 1, there was very little contaminating RNA migrating at a faster rate on the 1% agarose gel. The appearance of the expected high molecular weight bands from the undigested forms of the isolated DNA indicated that the isolated DNA was essentially intact and therefore, not degraded.

The appearance of a 'smear' of DNA above and below undigested DNA bands would be an indication of degraded DNA. As was observed in FIG. 1, there was no discernible 'smear' above and below the bands of DNA, thus, the isolated DNA appeared to be intact. This preparation of isolated DNA had very little RNA remaining as well.

Next, the ability of the isolated DNA to be successfully digested with selected restriction endonucleases was assessed. In these studies, the isolated DNA was digested with a predetermined restriction endonuclease overnight at 37° C. The enzyme treated DNA was then separated on an agarose gel (0.7%) and the gel electrophoresed in TAE buffer at 20 volts for 17 hours. The DNA was stained with ethidium bromide (500 µg/l in 1×TAE) and photographed under ultraviolet light. Hind II digested lambda and Hae III digested phi $\phi \times 174$ DNA were used for molecular weight markers.

The results of the foregoing restriction enzyme 2 analysis is shown in FIG. 2. As can be seen, the 'EF' DNA sample tested in this assay was capable of being digested significantly with each of the enzymes tested, including BamHi, BglII, EcoRI, HindIII, PstI and PvuII. The results shown in FIG. 2 should be compared to those shown for the undigested DNA sample, found in lane 5 of FIG. 1, which is believed to dramatically demonstrate the ability of the isolated DNA to be enzymatically digested.

EXAMPLE 3

Southern Blot of DNA Isolated from the Above Described Method

To test the functionality of the isolated DNA from the above protocol, a Southern blot may be performed. The isolated DNA is separated on an agarose gel, stained, photographed, transferred to nitrocellulose filter, probed with a radioactive indicator, washed, dried, exposed to x-ray film, developed and then analyzed for the proper cross reactivity depending on the indicator used.

EXAMPLE 4

Pulse Field Gel Electrophoresis on DNA Isolated with the Above Mentioned Protocol The DNA isolated by employing the above described protocol may further analyzed by pulse field electrophoresis. This gel system allows the investigator to analyze high molecular weight DNA (greater than 75 kilobases) for assessing its molecular weight. This size determination is done by comparing the isolated test DNA to DNA isolated from a control DNA exemplary techniques for performing suitable pulse field gel electrophoresis is set forth in reference 13.

The references listed below are incorporated herein by reference to the extent that they supplement, explain, provide a background for or teach methodology, techniques and/or compositions employed herein.

REFERENCES

1. Bahnak, Nucleic Acids Res., 16(3):1208–1211, 1988.

2. Gustafson et al., Analytical Biochemistry, 165:294-299, 1987.
3. Lippke et al., Applied Environmental Microbiology, 53:2588-2589, 1987.
4. Jeanpierre, Nucleic Acids Res., 15(22):9611-9612, 1987.
5. Holm et al., Gene, 42:169-173, 1986.
6. Hoffman et al., Gene, 57:267-272, 1987.
7. Krawetz et al., J. Biochemical and Biophysical Methods, 12:29-36, 1986.
8. Bowtell, Analytical Biochemistry, 162:463-465, 1987.
9. Miller et al., Nucleic Acids Res., 16(3):1215, 1988.
10. Chirgwin et al., Biochemistry, 18:5294, 1979.
11. Noll, et al., *Methods in Enzymology*, Volume XII, "Nucleic Acids", Part B, 129-160, 1968.
12. Lozzio, C.B. and Lozzio, B.B., Blood 45:321-334, 1975.
13. Lai et al. (198a), *Biotechnicues*, 7:34-42.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An efficient method for obtaining substantially intact, essentially protein-free nucleic acids from cells comprising the steps of:
   a) disrupting and lysing cells using a nucleic acid releasing composition having a chaotropic component to release the nucleic acids from the cells;
   b) precipitating the released nucleic acids from the lysed cells;
   c) resuspending the precipitated nucleic acids; and
   d) subjecting the resuspended nucleic acids to a polyanionic sulfated polysacchanide protein dissociating composition at a level effective to promote the dissociation of nucleic acid-associated proteins from the resuspended nucleic acids to obtain substantially intact nucleic acids free of strong interactions with contaminating proteins.

2. The method of claim 1, further comprising collecting the precipitated nucleic acids.

3. The method of claim 2, wherein collecting the precipitated nucleic acids comprises centrifuging the precipitated nucleic acids to form a pellet.

4. The method of claim 1, further comprising subjecting the dissociating composition-treated nucleic acids to digestion with a protease to digest proteins.

5. The method of claim 1, further comprising subjecting the dissociating composition-treated nucleic acids to digestion with an essentially DNAse-free RNAse to digest RNA.

6. The method of claim 1, further comprising subjecting the dissociated nucleic acids to digestion with a DNAse to digest DNA.

7. The method of claim 1, further comprising subjecting the dissociated nucleic acids to a concentration of ethanol effective to precipitate the nucleic acids.

8. The method of claim 1, further comprising washing the dissociated nucleic acids and placing the washed nucleic acids into a selected buffer.

9. The method of claim 1, wherein the isolated nucleic acid comprises DNA.

10. The method of claim 1, wherein the isolated nucleic acid comprises RNA.

11. The method of claim 1, wherein the cells are obtained from blood components or solid tumor tissue biopsy samples.

12. The method of claim 1, wherein the chaotropic component of the nucleic acid releasing composition comprises guanidine hydrochloride or guanidinium isothiocyanate.

13. The method of claim 12, wherein the chaotropic component comprises guanidine hydrochloride.

14. The method of claim 12, wherein the chaotropic component comprises guanidinium isothiocyanate.

15. The method of claim 1, wherein the nucleic acid releasing composition further includes a detergent.

16. The method of claim 15, wherein the detergent comprises a surface-active agent of the anionic type.

17. The method of claim 16, wherein the anionic surface-active detergent comprises sodium dodecyl sulfate.

18. The method of claim 16, wherein the anionic surface-active detergent comprises sarcosyl.

19. The method of claim 1, wherein the nucleic acid releasing composition further includes a sulfhydryl reducing agent.

20. The method of claim 19, wherein the sulfhydryl reducing agent comprises 2-mercaptoethanol or DTT.

21. The method of claim 1, wherein the nucleic acid releasing composition which further includes a level of salt effective to promote dissociation of proteins from the nucleic acids.

22. The method of claim 21, wherein the level of salt effective to promote dissociation of proteins from the nucleic acids comprises salt in a concentration ranging from about 0.1M to 0.9M.

23. The method of claim 22, wherein the level of salt further includes salt in a concentration ranging from about 0.4M to 0.6M.

24. The method of claim 21, wherein the salt comprises sodium chloride, sodium acetate, potassium acetate or ammonium acetate.

25. The method of claim 1, wherein the polyanion-containing protein-dissociating composition comprises a sulfated polysaccharide in a concentration ranging from about 100 micrograms to 1500 micrograms/ml.

26. The method of claim 25, wherein the level of sulfated polysaccharide comprises sulfated polysaccharide in a concentration ranging from about 200 micrograms to 800 micrograms/ml.

27. The method of claim 25, wherein the sulfated polysaccharide comprises heparin or heparitin sulfate.

28. The method of claim 25, wherein the sulfated polysaccharide comprises heparin.

29. The method of claim 25, wherein the sulfated polysaccharide comprises heparitin sulfate.

30. The method of claim 28, wherein the sulfated polysaccharide comprises sodium heparin.

31. The method of claim 28, wherein the sulfated polysaccharide comprises lithium heparin.

32. The method of claim 25, wherein the polyanion-containing component further includes phosphate in a concentration ranging from about 0.1 mM to 25 mM.

33. A method for isolating nucleic acids from cells, comprising the steps of:

a) disrupting and lysing the cells, thereby releasing nucleic acids which are complexed to proteins, using a composition containing guanidine hydrochloride or guanidinium isothiocyanate, at a concentration ranging from about 3M to 8M, and said composition furthers contains sodium acetate or sodium chloride at a concentration ranging from 0.01M to 0.6M b) precipitating the released nucleic acids from the lysed cells;

c) resuspending the precipitated nucleic acids in a selected buffer;

d) dissociating the proteins from the resuspended nucleic acids using a composition containing a sulfated polysaccharide comprised of either heparin or heparitin sulfate at a concentration ranging from about 0.1 milligrams to about 1.0 milligram per milliliter and said composition further contains phosphate in a concentration ranging from about 0.1 mM to about 25 mM; and f) collecting the isolated and partially purified nucleic acids wherein collecting comprises centrifuging the nucleic acids to form a pellet and dissolving the pellet in a selective buffer for further processing.

* * * * *